United States Patent [19]

DeBernardis et al.

[11] Patent Number: 4,622,405
[45] Date of Patent: Nov. 11, 1986

[54] 1,2,3,3A,8,8A-HEXAHYDRO-INDENO[1,2-C]PYRROLES USEFUL IN THE TREATMENT OF HYPERTENSION

[75] Inventors: John F. DeBernardis, Lake Villa; Martin Winn, Deerfield, both of Ill.

[73] Assignee: Abbott Laboratories, North Chicago, Ill.

[21] Appl. No.: 695,520

[22] Filed: Jan. 28, 1985

Related U.S. Application Data

[63] Continuation-in-part of Ser. No. 634,235, Jul. 25, 1984, abandoned.

[51] Int. Cl.⁴ .................. C07D 209/56; A61K 31/40
[52] U.S. Cl. ................................. 548/427; 514/411
[58] Field of Search ..................... 548/427; 514/411

[56] References Cited

U.S. PATENT DOCUMENTS 4,164,583 8/1979 Achini et al. ..................... 548/427
4,370,341 1/1983 Asselin et al. ..................... 548/427
4,505,932 3/1985 DeBernardis et al. ............ 514/649

FOREIGN PATENT DOCUMENTS 95666 12/1983 European Pat. Off. ............ 548/427

OTHER PUBLICATIONS

Asratyan et al, Chem. Abst., 87-84762g.
Alexander et al, Chem. Abst., 97-625k.
Horning et al, JACS, 73; 5826, 1956.
Merck Index, 9th edition, 2925, Methyldopa.
Merck Index, 9th edition, 2353, Clonidine.

Primary Examiner—Donald G. Daus
Assistant Examiner—Cecilia Shen
Attorney, Agent, or Firm—Steven F. Weinstock; Martin L. Katz

[57] ABSTRACT

Disclosed herein are 1,2,3,3a,8,8a-hexahydro-indeno[1,2-c]pyrroles represented by the formula

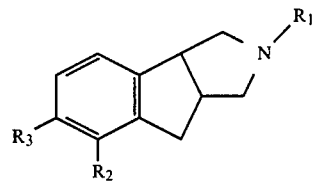

wherein $R_1$ is hydrogen, loweralkyl of 1 to 5 carbon atoms, arylalkyl, loweracyl or benzoalkylenedioxy; $R_2$ and $R_3$ may be the same or different and are hydroxy, loweralkoxy, halo, thiomethyl, loweracyl, $NR_4R_5$, $NHSO_2R_6$ or arylalkoxy or $R_2$ and $R_3$ taken together may form a methylenedioxy or ethylenedioxy bridge; $R_4$ and $R_5$ may be the same or different and are hydrogen, loweralkyl of 1 to 2 carbon atoms or loweracyl; and $R_6$ is hydrogen or loweralkyl of 1 to 2 carbon atoms.

3 Claims, No Drawings

1,2,3,3A,8,8A-HEXAHYDRO-INDENO[1,2-C]PYRROLES USEFUL IN THE TREATMENT OF HYPERTENSION

BACKGROUND

This application is a continuation-in-part of U.S. patent application, Ser. No. 634,235, filed July 25, 1984, now abandoned.

TECHNICAL FIELD

This invention relates to novel 1,2,3,3a,8,8a-hexahydro-indeno[1,2-c]pyrroles useful in the treatment of hypertension.

The adrenergic nervous system plays a major role in the innervation of heart, blood vessel and smooth muscle tissue. Agents capable of interacting with receptor sites within the adrenergic nervous system can result in a variety of physiological responses, including vasoconstriction, vasodilation, and increased or decreased heart rate (chronotropic), contractility (inotropic) and metabolic activity. In the past, various adrenergic agents have been employed to affect these and other physiological responses. However, it is highly desirable to obtain new adrenergic agents which demonstrate a high degree of specificity for differing receptor types within the adrenergic nervous system in order to obtain a desired physiological response separate from other possible, and perhaps less desirable, responses of the system. This property has been lacking from most previously employed adrenergic agents. Thus, the search continues for new and improved adrenergic agents capable of selective interaction with adrenergic receptor sites.

It has now been determined that a new class of compounds, the 1,2,3,3a,8,8a-hexahydro-indeno[1,2-c]pyrroles, as herein defined, demonstrate an ability to interact specifically with various adrenergic receptor types and are useful in the treatment of hypertension.

DISCLOSURE OF THE INVENTION

The present invention provides 1,2,3,3a,8,8a-hexahydro-indeno[1,2-c]pyrroles represented by the formula

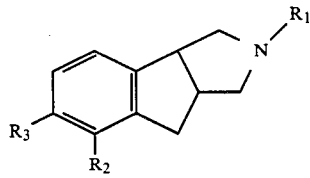

wherein $R_1$ is hydrogen, loweralkyl of 1 to 3 carbon atoms, arylalkyl, loweracyl or benzoalkylenedioxy; $R_2$ and $R_3$ may be the same or different and are hydroxy, loweralkoxy, halo, thiomethyl, loweracyl, $NR_4R_5$, $NHSO_2R_6$ or arylalkoxy or $R_2$ and $R_3$ taken together may form a methylenedioxy or ethylenedioxy bridge; $R_4$ and $R_5$ may be the same or different and are hydrogen, loweralkyl of 1 to 2 carbon atoms or loweracyl; and $R_6$ is hydrogen or loweralkyl of 1 to 2 carbon atoms.

As used herein, the terms "loweralkyl of 1 to 3 carbon atoms" refers to straight or branched chain saturated hydrocarbon radicals having 1 to 3 carbon atoms, such as methyl, ethyl, n-propyl, iso-propyl, and the like. The term additionally includes halo-substituted loweralkyl radicals such as, for example, trifluoromethyl, 2-trichloroethyl, and the like.

As used herein, the term "loweralkyl of 1 to 2 carbon atoms" refers to methyl or ethyl.

As used herein, the term "loweralkoxy" refers to methoxy or ethoxy.

As used herein, the terms "arylalkyl" and "arylalkoxy" refer to loweralkyl of 1 to 5 carbon atoms or loweralkoxy of 1 to 5 carbon atoms substituted phenyl compounds, respectively, including but not limited to benzyl, phenethyl, phenpropyl and phenbutyl or benzoxy, phenoxy, phenethoxy, phenpropoxy and phenbutoxy, respectively.

As used herein, the term "halo" means chloro, bromo, fluoro and iodo.

As used herein, the term "loweracyl" means an acyl group represented by the formula

wherein R is loweralkyl of 1 to 5 carbon atoms as herein defined. Illustrative acyl groups useful in the practice of the invention are acetyl, n-propionyl, n-butyryl, s-butyryl, iso-butyryl, and the like.

As used herein, the term "benzoalkylenedioxy" refers to the structure:

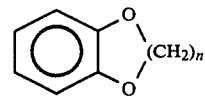

wherein n=1 or 2.

The term "pharmaceutically acceptable salts" refers to the pharmaceutically acceptable, relatively nontoxic, inorganic or organic acid addition salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitrate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salt of this invention can be per-N-salts.

The foregoing may be better understood in connection with the following examples:

EXAMPLE 1

4,5-Dimethoxy indane, 1,2-dicarboxylic acid diethyl ester 88.9 g. 4,5-dimethoxy indene, 1,2-dicarboxylic acid, diethyl ester (J.A.C.S. 73 5826, 1956) in 1 liter ethanol was hydrogenated over 120 g. Raney Nickel catalyst at 3 atmospheres pressure. The catalyst was filtered and the solution concentrated to give 85 g. product as an oil.

EXAMPLE 2

4,5-Dimethoxy indane, 1,2-dicarboxylic acid 45.8 g. of the diethyl ester of Example 1, 60 ml. ethanol, 90 ml. water, and 69 g. 45% potassium hydroxide (KOH) were refluxed 1 hour. The solution was concentrated in vacuum and acidified with hydrochloric acid. The resulting solid was filtered and dissolved in dimethoxyethane. The solution was dried over magnesium sulfate (MgSO$_4$), concentrated and benzene added, to get the desired product, 35.06 g., m.p. 153°–160° C.

Analysis, theoretical: C, 58.64; H, 5.30. Found: C, 58.40; H. 5.39.

EXAMPLE 3

4,5-Dimethoxy indane, 1,2-dicarboxylic acid anhydride 5.00 g. of the dicarboxylic acid of Example 2, 50 ml. acetic anhydride and 50 mg. toluene sulfonic acid monohydrate were refluxed for 1 hour. The acetic anhydride was removed on the rotovac and the residue distilled to give 4.13 g. product, b.p. 190°–195° C./0.3 mm Hg.

EXAMPLE 4

2-Benzyl-6,7-dimethoxy-1,2,3,3a,8,8a-hexahydro-indeno[1,2-c]pyrrole-1,3-dione 4.00 g. of the resultant anhydride of Example 3 was suspended in 80 ml. xylene, then 1.90 g. benzylamine was added. The mixture was refluxed 3 hours. Benzene (60 ml) was added to the cooled solution and a small amount of solid was filtered. The benzene filtrate was washed with dilute hydrochloric acid and then with dilute potassium bicarbonate. After drying (MgSO$_4$), and concentrating, ether was added to get 4.50 g. product, m.p. 130°–132° C. (83% yield).

Analysis, theoretical: C, 71.20; H, 5.68; N, 4.15 Found: C, 71.01; H, 5.62; N, 4.21.

EXAMPLE 5

2-Benzyl-6,7-dimethoxy-1,2,3,3a,8,8a-hexahydro-indeno[1,2-c]pyrrole hydrochloride 6.19 g. of the resultant compound of Example 4 suspended in 15 ml. tetrahydrofuran (THF) was treated with 110 ml. 1M BH$_3$ in THF under nitrogen atmosphere. The solution was refluxed 4 hours, then cooled and a solution of 35 ml. concentrated hydrochloric acid and 35 ml. water was added slowly. The solution was refluxed for 20 minutes and then concentrated in vacuum. The residue was made basic with potassium hydroxide solution and extracted with chloroform. The chloroform extracts were dried (K$_2$CO$_3$) and concentrated. The residue was acidified with HCl in isopropyl alcohol and this solution was concentrated. Acetonitrile was added to give the product 5.78 g., m.p. 176°–178° C.

Analysis, theoretical: C, 69.40; H, 6.99; N, 4.05. Found: C, 69.01; H, 7.03; N, 3.98.

EXAMPLE 6

6,7-Dimethoxy-1,2,3,3a,8,8a-hexahydro-indeno[1,2-c]pyrrole hydrochloride 4.36 g. of the resultant compound of Example 5 was hydrogenated with 0.9 g. 5% Pd/C in 100 ml. methanol at 3 atmospheres, affording 2.95 g. of product (92%), m.p. 176°–178° C.

Analysis, theoretical (with ¼H$_2$O): C, 60.22; H, 6.80; N, 5.40. Found: C, 60.00; H, 6.91, N, 5.42.

EXAMPLE 7

1,2,3,3a,8,8a-Hexahydro-indeno[1,2-c]pyrrole 6,7-diol hydrobromide 2.00 g. of the resultant compound of Example 6 in 13 ml. CH$_2$Cl$_2$ under a nitrogen atmosphere at −78° C. was treated with 10 g. boron tribromide (BBr$_3$). The mixture was stirred at 0° C. for 1 hour and then cooled to −78° C. while 50 ml. methanol was added slowly. The solution was concentrated in vacuum and the residue was crystallized from acetonitrile to get 1.97 g. product, m.p. 206°–208° C.

Analysis, theoretical: C, 48.55; H, 5.18; N, 5.15. Found: C, 48.26; H, 5.16; N, 5.11.

EXAMPLE 8

6,7-Dimethoxy-2-methyl-1,2,3,3a,8,8a-hexahydro-indeno[1,2-c]pyrrole hydrochloride 1.50 g. of the resultant compound of Example 6, 0.15 g. 5% Pd/C in 95 ml. methanol, 5 ml. 37% formaldehyde and 0.8 g. sodium acetate were hydrogenated at 3 atmospheres. The solution was concentrated after removal of the catalyst and the residue was made basic with KOH in water. This was extracted with CHCl$_3$, dried (K$_2$CO$_3$) and concentrated. The residue was dissolved in acetonitrile and acidified with hydrochloric acid in ether to get 1.40 g. product, m.p. 160°–162° C.

Analysis, theoretical: C, 62.33; H, 7.47; N, 5.19. Found: C, 62.27; H, 7.49; N, 5.28.

EXAMPLE 9

2-Methyl-1,2,3,3a,8,8a-hexahydro-indeno[1,2-c]pyrrole-6,7-diol hydrobromide 1.81 g. of the resultant compound of Example 8 was treated with BBr$_3$ as described in Example 7 to get 1.85 g. product, m.p. 191°–193° C.

Analysis, theoretical (with ¼ water): C, 49.58; H, 5.72; N, 4.82. Found: C, 49.78; H, 5.63; N, 4.76.

EXAMPLE 10

2-Acetyl-6,7-dimethoxy-1,2,3,3a,8,8a-hexahydro-indeno[1,2-c]pyrrole 1.36 g. of the resultant compound of Example 6 was basified with KOH in water and extracted into ether. The ether was evaporated and the residue dissolved in 5 ml. CHCl$_3$ and treated with 1.7 ml. acetic anhydride. After refluxing for 10 minutes, the solution was concentrated and the excess acetic anhydride decomposed with KOH in water. The residue was extracted with CHCl$_3$, dried (MgSO$_4$) and concentrated to give 1.5 g. product which was used directly in the next step (Example 11).

EXAMPLE 11

2-Ethyl-6,7-dimethoxy-1,2,3,3a,8,8a-hexahydro-indeno[1,2-c]pyrrole hydrochloride The resultant compound of Example 10 was dissolved in 15 ml. THF and this solution was added to a suspension of 0.6 g. LiAlH$_4$ in 8 ml. THF. The reaction mixture was refluxed 3 hours and worked up with 1 ml. water and 1.5 ml. 25% NaOH. Concentrating the THF solution yielded the amine as an oil. The hydrochloride was made with hydrochloric acid in CH$_2$Cl$_2$ and was used without further purifition.

EXAMPLE 12

2-Ethyl-1,2,3,3a-8,8a-hexahydro-indeno[1,2-c]pyrrole-6,7-diol hydrobromide

The product of Example 11 was treated with BBr$_3$ as described in Example 7 to give 620 mg. product, m.p. 195°–198° C.

Analysis, theoretical (for ⅓ water): C, 59.65; H, 7.15; N, 5.35. Found: C, 59.67; H, 7.15; N, 5.29.

EXAMPLE 13

2-Propyl-1,2,3,3a,8,8a-hexahydro-indeno[1,2-c]pyrrole-6,7-diol hydrobromide

The compound of Example 6 (4.00 g.) was converted in 92% yield to the N-propionyl amide by the method of Example 10. This was reduced to the amine in 65% yield by the method in Example 11 and this was demethylated with $BBr_3$ by the method of Example 7 in 80% yield to give the desired product, m.p. 192°–195° C.

Analysis, theoretical: C, 53.50; H, 6.42; N, 4.46. Found: C, 53.14; H, 6.36; N, 4.44.

The therapeutic activity of the compounds can be demonstrated in vivo by their ability to decrease arterial blood pressure and/or heart rate in the spontaneously hypertensive rat as follows: A group of Okamoto rats, which develop hypertension spontaneously when reaching young adulthood, are deprived of food for a period of 16 hours and are placed in semi-restraining wire mesh cylinders maintained at a constant temperature of 36° C. An occluding cuff, operatively connected to a programmed sphygmomanometer, is placed over the tail of each rat of the group and retained near the tail base. The pressure of each cuff is automatically, cyclically increased within the range of from 0 to 250 mm Hg. at the rate of 10 mm Hg./sec., the total inflation and deflation time of each cycle being 50 seconds, with a 10 second rest period between cycles. A photocell is placed distal to the cuff to detect pulses resulting from the forward motion of blood flow with each heartbeat of the rat. As the pressure in the cuff increases, measurable pulses disappear at the point where the cuff pressure equals the arterial blood pressure. Measurable pulses reappear during deflation at approximately the same pressure, and arterial blood pressure is thereby established by cuff pressure at the point of pulse appearance. The heart rate is determined from the arterial pulse wave. A 100 mg/kg dose of a test compound of Formula I is administered orally to each rat of the test group, and five interference-free signals are recorded on a Model 7 Grass polygraph for each rat at various measurement periods following administration. By following the foregoing procedure, the tested preferred compounds of the invention are shown to decrease the arterial blood pressure and/or heart rate of rats of the group.

The compounds of the invention can be administered in any effective pharmaceutically acceptable form to warm blooded animals, e.g., in oral, parenteral or infusable dosage forms, or as a buccal or nasal spray. Suitable parenteral routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying and dispersing agents. They may be sterilized, for example, by filtration through a bacteria-retaining filter, or by incorporating sterilizing agents into the compositions. They can also be manufactured in the form of sterile solid compositions which can be dissolved in sterile water, or other sterile injectable medium, immediately before use.

Solid dosage forms for oral administration include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, dosage levels of about 0.1 to about 200, more preferably about 0.5 to about 150 and most preferably about 1 to about 125 mg of active ingredient per kg of body weight per day are administered orally to a mammalian patient suffering from hypertension. If desired, the daily dose may be divided into multiple doses for administration, e.g., two to four separate doses per day.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

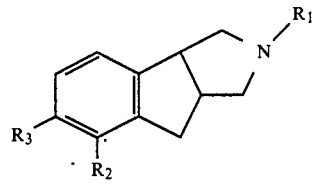

wherein $R_1$ is hydrogen, loweralkyl of 1 to 3 atoms, phenloweralkyl, loweracyl or benzoalkylenedioxy; $R_2$ and $R_3$ may be the same or different and are hydroxy, loweralkoxy, halo, thiomethyl, loweracyl, $NR_4R_5$, $NHSO_2R_6$ or phenloweralkoxy or $R_2$ and $R_3$ taken together may form a methylenedioxy or ethylenedioxy bridge; $R_4$ and $R_5$ may be the same or different and are hydrogen, loweralkyl of 1 to 2 carbon atoms or loweracyl; and $R_6$ is hydrogen or loweralkyl of 1 to 2 carbon atoms or a pharmaceutically acceptable salt thereof.

2. The compound of claim 1 wherein $R_1$ is hydrogen, loweralkyl of 1 to 3 carbon atoms, loweracyl or benzyl.

3. The compound of claim 1 wherein $R_2$ and $R_3$ may be the same or different and are hydroxy or methoxy.

* * * * *